US011702309B2

(12) United States Patent
Spurzem

(10) Patent No.: US 11,702,309 B2
(45) Date of Patent: Jul. 18, 2023

(54) TURNING DEVICE FOR A PRODUCTION LINE FOR HYGIENE PRODUCTS

(71) Applicant: Winkler + Dünnebier GmbH, Neuwied (DE)

(72) Inventor: Heinrich Spurzem, Mayen (DE)

(73) Assignee: Winkler + Dünnebier GmbH, Neuwied (DE)

( * ) Notice: Subject to any disclaimer, the term of this patent is extended or adjusted under 35 U.S.C. 154(b) by 35 days.

(21) Appl. No.: 17/177,355

(22) Filed: Feb. 17, 2021

(65) Prior Publication Data
US 2021/0253369 A1 Aug. 19, 2021

(30) Foreign Application Priority Data
Feb. 18, 2020 (DE) ...................... 10 2020 104 275.2

(51) Int. Cl.
*B65H 29/24* (2006.01)
*B65G 47/91* (2006.01)
*A61F 13/15* (2006.01)

(52) U.S. Cl.
CPC ..... *B65H 29/241* (2013.01); *A61F 13/15764* (2013.01); *A61F 13/15804* (2013.01);
(Continued)

(58) Field of Classification Search
None
See application file for complete search history.

(56) References Cited

U.S. PATENT DOCUMENTS

2016/0376109 A1 12/2016 Schneider et al.
2020/0345559 A1* 11/2020 Inoue ...................... B65H 35/08

FOREIGN PATENT DOCUMENTS

WO 2015079367 A1 6/2015
WO 2019215547 A1 11/2019

* cited by examiner

*Primary Examiner* — Barbara J Musser
(74) *Attorney, Agent, or Firm* — Rankin, Hill & Clark LLP

(57) ABSTRACT

The invention relates to a turning apparatus for a production plant (2) for sanitary products, in particular adult or baby diapers, the turning apparatus having a drum (12) which rotates about a geometrical drum rotational axis (11), and at least one plate (14) which is spaced apart radially from the drum rotational axis (11) and is coupled to the drum (12), which plate (14) comprises a suction face (15) for the transport of sanitary material pieces (16), which suction face (15) holds the respective sanitary material piece (16) by means of a vacuum during the transport, the plate (14) having a geometrical vertical axis (17) which runs radially with respect to the drum rotational axis (11), the plate (14) receiving the sanitary material piece (16) with a first orientation about the vertical axis (17) in a first transfer region (18), and transporting the sanitary material piece (16) from the first transfer region (18) to a second transfer region (20) along a setpoint transfer path (19) which runs in the circumferential direction around the drum rotational axis (11), the suction face (15) being rotated with the sanitary material piece (16) about the vertical axis (17) during the transport, the plate (14) outputting the sanitary material piece (16) in the second transfer region (20) with a second orientation which is different than the first orientation about the vertical axis (17). It is proposed that, during the receiving and/or outputting, the plate (14) carries out a non-linear compensation movement relative to the drum (12) with a radial movement component.

15 Claims, 4 Drawing Sheets

(52) U.S. Cl.
CPC ........ *B65G 47/915* (2013.01); *B65H 2402/30* (2013.01); *B65H 2403/512* (2013.01); *B65H 2406/3454* (2013.01); *B65H 2801/57* (2013.01)

a)

b)

c)

TURNING DEVICE FOR A PRODUCTION LINE FOR HYGIENE PRODUCTS

The invention relates to a turning apparatus for a production plant for sanitary products, in particular adult or baby diapers, and to a production plant for sanitary products per se.

Sanitary products are understood to mean absorbent elements which are used close to the body, in particular adult or baby diapers, incontinence pads and pants, sanitary towels, panty liners or the like. It is usually a common feature of sanitary products that they have a liquid-absorbing core as sanitary material which is fastened to a carrier material. The carrier material can be configured, in particular, by way of a body-side material layer (top sheet) and a material layer which is remote from the body (back sheet). Lateral fastening elements (wings) can be attached thereto, which lateral fastening elements serve to fasten the sanitary product to the body.

Production plants for sanitary products usually have a machine running direction, along which both the sanitary material and the carrier material are guided. If the sanitary material and the carrier material are to be connected, however, the sanitary material usually has to be rotated by 90°, in order to be positioned correspondingly transversely with respect to the carrier material. For this purpose, in the case of known production plants, the sanitary material is cut and is turned by a turning apparatus.

In the case of a known turning apparatus (WO 2019/215547 A1), the cutting of the sanitary material is likewise carried out on the turning apparatus. This has the disadvantage that it is not readily possible to produce various formats, that is to say sizes, of the sanitary products by way of one and the same turning apparatus. In the case of other known production plants, the cutting operation is therefore carried out upstream of the turning apparatus. It is a problem, however, that displacements and rejects can occur during the transfer of the cut sanitary material pieces to the turning apparatus and from the turning apparatus. Known turning apparatuses have curved plates for receiving the sanitary material pieces, which curved plates are adapted to a transfer track of the usually rotating turning apparatus. Since said plates are rotated, however, a flat transfer thus cannot be achieved both in the case of the receiving and in the case of the outputting of the sanitary material pieces.

A linear compensation movement takes place in the case of a further known turning apparatus (US 2016/0376109 A1). This is, however, firstly structurally complicated, since high tolerances have to be maintained, and secondly the adaptation to the circular transfer tracks of the production plant is not possible.

The invention is based on the problem of configuring and developing the known turning apparatuses in such a way that an increased precision during the transfer is achieved, with the retention of the possibility of producing various formats.

The above problem is solved in the case of a turning apparatus in accordance as claimed herein.

The invention proceeds fundamentally from a turning apparatus with a drum, which rotates about a geometrical drum rotational axis, and at least one plate, which is spaced apart radially from the drum rotational axis and is coupled to the drum. The plate comprises a suction face for the transport of sanitary material pieces, which suction face holds the respective sanitary material piece by means of a vacuum during the transport. Furthermore, the plate has a geometrical vertical axis which runs radially with respect to the drum rotational axis. Furthermore, the plate receives the sanitary material piece with a first orientation about the vertical axis in a first transfer region, and transports the sanitary material piece from the first transfer region to a second transfer region along a setpoint transfer path which runs in the circumferential direction around the drum rotational axis, the suction face being rotated with the sanitary material piece about the vertical axis during the transport. The plate outputs the sanitary material piece in the second transfer region with a second orientation which is different than the first orientation about the vertical axis.

The fundamental consideration is essential that the plate can be adapted to the transfer in an active manner by means of a compensation movement. As a result of said compensation movement, it is no longer merely the shape of the plate which is decisive for the contact between the plate and the sanitary material piece during the transfer. As a result, rotatable plates can also transfer the sanitary material piece precisely, without being limited by way of the restricted possibilities of the configuration of the surface of the suction face.

It is proposed in detail that, during the receiving and/or outputting, the plate carries out a non-linear compensation movement relative to the drum with a radial movement component.

In a refinement, the compensation movement of the plate additionally has a movement component in the circumferential direction about the drum rotational axis, as a result of which more complex compensation movements are made possible. The latter can be adapted more precisely to the speed of the turning apparatus and a further part of the production plant otherwise which receives or outputs the sanitary material piece, and to the geometrical conditions of the turning apparatus and the receiving and outputting part of the production plant.

For an implementation which is simple, in particular, in mechanical terms, it can be provided that the plate is coupled to the drum in such a way that the progress of the compensation movement is dependent on a rotational angle of the drum about the drum rotational axis.

A refinement which is particularly suitable for the conditions of the transfer in the case of customary turning apparatuses, the plate forms, with the drum, a coupling mechanism.

In particular for the actuation of the coupling mechanism, it can be provided in the case of one refinement that the plate is coupled to a cam disk by means of a guide member. As a result, a possibility which is not particularly complicated in structural terms is specified for carrying out compensation movement.

In a further preferred refinement of the compensation movement, which refinement is relatively simple to implement, the compensation movement is a rotation of the plate about a geometric rotational axis which preferably runs parallel, but not coaxially, with respect to the drum rotational axis.

In a refinement, the receiving and/or outputting of the sanitary material piece take/takes place over the full surface area and/or at a constant speed. A situation can thus be achieved where considerably fewer displacements and rejects of the sanitary material piece occur in comparison with known turning apparatuses, as a result of which the production accuracy of the production plant increases.

In one particularly preferred refinement, the suction face of the plate is planar along its first and/or second orientation. A transfer over the full surface area with any desired orientation can be achieved by way of the omission of the curved suction faces of the plate.

In the case of one refinement, a part of the suction face, which part is situated in the first and/or second transfer region, runs radially within the setpoint transfer path on account of the compensation movement during the receiving and/or outputting. This can preferably not be the case outside the first and/or second transfer region.

In order to activate a vacuum of the suction face, which vacuum generates the suction action, precisely where it is needed, it can be provided that the suction face comprises a plurality of suction segments. Said suction segments can be capable of being actuated individually and/or in groups, by way of which a situation can be achieved where the sanitary material piece is not attracted by suction by suction segments, with which it is not yet in contact or no longer has to be in contact. Furthermore, this is advantageous with regard to the energy efficiency.

According to further preferred refinements of the drum, the drum has a drive shaft for the production of the rotation of the drub about the rotational axis, and the vacuum is conducted from a vacuum source through the drive shaft to the suction face. The turning apparatus can have a plurality of identical plates.

In accordance with a further teaching which is given independent significance, a production plant for sanitary products with a turning device is proposed. Reference may be made to all comments with respect to the turning apparatus according to the proposal.

Preferred refinements of the production plant, with which preferred refinements the turning apparatus according to the proposal can be used particularly advantageously, are claimed herein.

In the following text, the invention will be described in greater detail on the basis of a drawing which shows merely one exemplary embodiment and in which:

FIG. 1 shows the turning apparatus 1 according to the proposal for a production plant 2 for sanitary products, in particular adult or baby diapers. Reference is made to the introductory part of the description with regard to other possible sanitary products.

Figure 2:
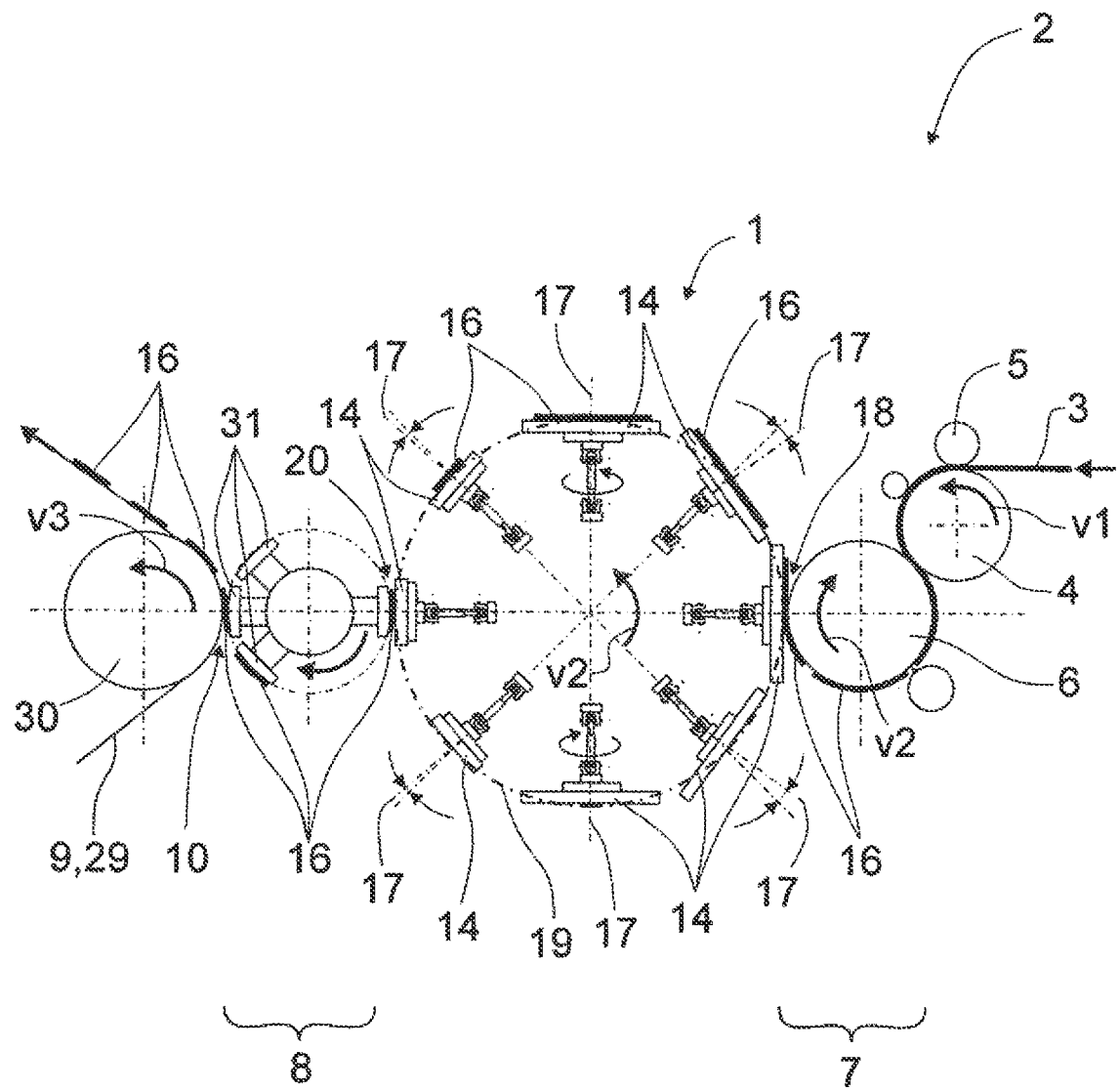

FIG. 2 diagrammatically shows the construction of a preferred production plant 2. A sanitary material web 3 is fed to the production plant 2 from the right in FIG. 2, and comes into contact there with a first transport roller 4 with a cross-sealing means 5. Here and preferably, the sanitary material is configured to be flat and/or as absorbent material.

Here, said first transport roller 4 can have a first speed v1 during operation. From there, the sanitary material web 3 can be transferred to a cutting roller 6 of a cutting unit 7, which cutting roller 6 rotates at a speed v2. The cutting unit 7 has a cutting device, for example a cutting blade, which cuts the sanitary material web 3. The cut sanitary material is at the same time separated by way of the slip which is produced on account of the different speeds v1 and v2 between the first roller 4 and the cutting roller 6. It is then transferred further to the left in FIG. 2 by the turning device 1 which is still to be described, and is turned in the process, is received by a repitch unit 8, that is to say a speed change unit, and is accelerated to a speed v3 and is combined with the carrier material 9 at a "marriage point" 10. The reason why the cut sanitary material is turned is usually that the sanitary material web 3 and the carrier material 9 run in parallel in a machine direction along the production plant 2, but are to be combined transversely with respect to one another.

Figure 1:
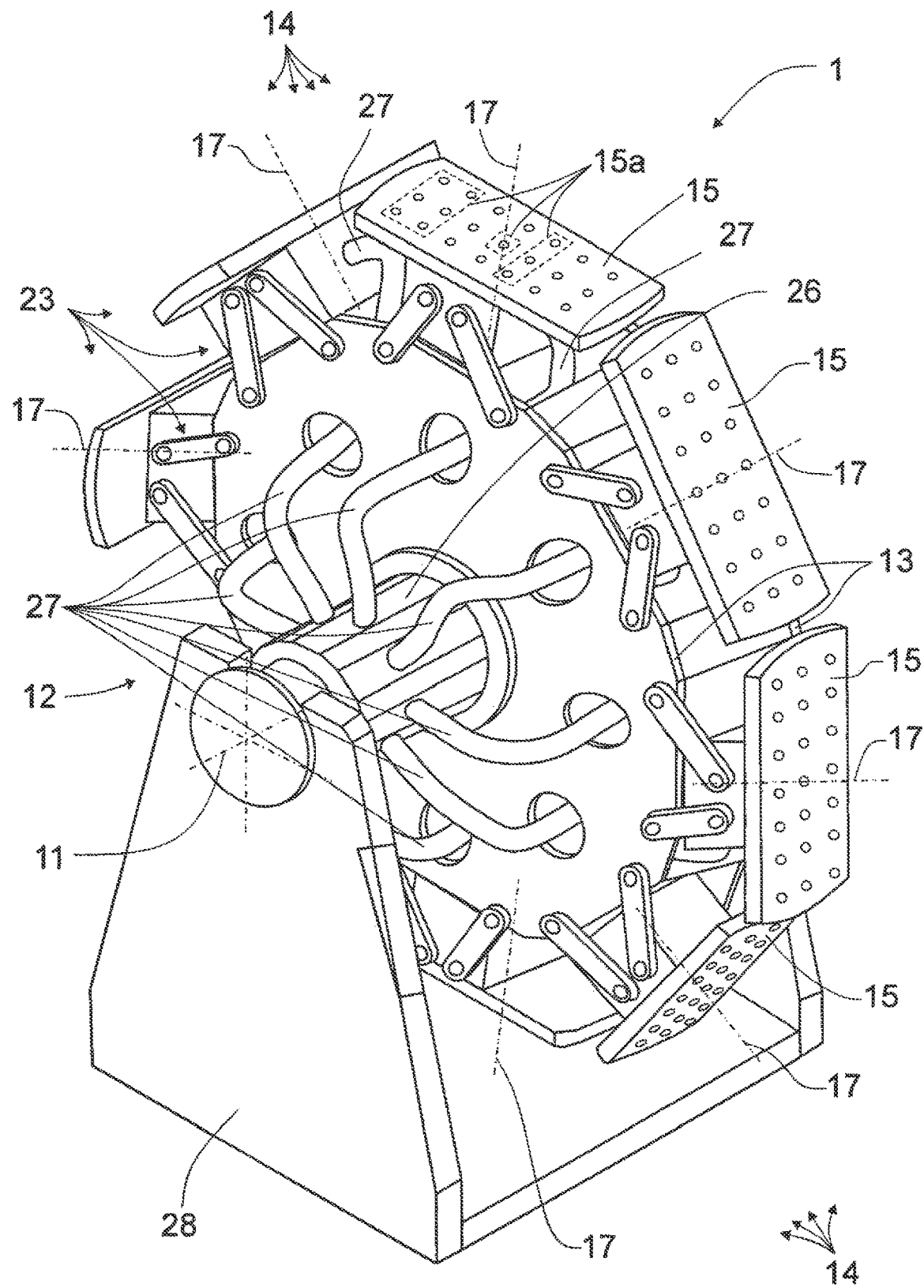
FIG. 1 shows the turning apparatus according to the proposal in a three-dimensional view from the outside, FIG. 2 diagrammatically shows the production plant including the process of manufacturing.

FIG. 1 shows the turning apparatus 1 according to the proposal in an outer view. The turning apparatus 1 has a drum 12 which rotates about a geometrical drum rotational axis 11. The term "drum" is to be understood broadly here; in the simplest case, the drum 12 can be a disk 13. A shell is not absolutely necessary in the case of the drum 12, but can fundamentally be provided. In the simplest case, the drum 12 also serves merely for mechanical fastening and guidance, and accordingly does not have to have any specific properties apart from those of a carrier. The drum 12 rotates endlessly here and preferably.

The turning apparatus 1 has at least one plate 14 which is spaced apart radially from the drum rotational axis 11 and is coupled to the drum 12. Here and preferably, the turning apparatus 1 has more than one plate 14 of this type. In the exemplary embodiment, the turning apparatus 1 has eight plates 14. In the following text, most of the comments relate for the sake of simplicity only to one plate 14. Here and preferably, however, the plates 14 are identical. Therefore, all comments in respect of the one plate 14 also apply to the other plates 14 correspondingly.

In the following text, some features of the turning apparatus 1 are described by way of the term "radial" and by way of the term "circumferential direction". Said terms always relate to the drum rotational axis 11.

The plate 14 and the drum 12 are coupled in terms of movement with regard to the rotation about the drum rotational axis 11, with the result that the plate 14 rotates with the drum 12 about the drum rotational axis 11. Here and preferably, the plate 14 and the drum 12 are coupled in terms of movement without slip with regard to the rotation about the drum rotational axis 11.

The plate 14 comprises a suction face 15 for the transport of sanitary material pieces 16. The suction face 15 holds the respective sanitary material piece 16 by means of a vacuum during the transport. The sanitary material piece 16 can thus also be transported transversely or perpendicularly with respect to the direction of gravity. Here and preferably, as has already been described, the sanitary material piece 16 was cut from the sanitary material web 3 by the production plant 2 by way of the cutting unit 7.

The plate 14 has a geometrical vertical axis 17 which runs radially with respect to the drum rotational axis 11. Said vertical axis 17 is defined with regard to the suction face 15 of the plate 14 and can, as will be explained later, be capable of being tilted, in particular, with regard to the drum rotational axis 11.

During operation, the plate 14 receives the sanitary material piece 16 with a first orientation about the vertical axis 17 in a first transfer region 18. The plate 14 transports the sanitary material piece 16 along a setpoint transfer path 19 which runs in the circumferential direction about the drum rotational axis 11 from the first transfer region 18 to a second transfer region 20. This can be best gathered from the illustration in FIG. 3. The setpoint transfer path 19 is, in particular, circular and specifies, in relation to the center point of the sanitary material piece 16, along where the sanitary material piece 16 is transported. Here and preferably, the setpoint transfer path 19 is defined by way of the maximum radially present space in the first transfer region 18 and in the second transfer region 20. Here and preferably, the first transfer region 18 and/or the second transfer region 20 are/is linear or even virtually punctiform in cross section, as shown in FIG. 2. The transfer regions 18, 20 are defined as those regions, in which the sanitary material piece 16 is situated during the transfer. Since said regions are not identical in the case of every sanitary material piece 16 as a result of tolerances, not every sanitary material piece 16 utilizes the full transfer region 18, 20 during its transfer.

The suction face 15 with the sanitary material piece 16 is rotated about the vertical axis 17 during the transport. Here and preferably, said rotation takes place by 90°. Here and preferably, moreover, the rotation takes place temporally and spatially during the transport and, in particular, from an orientation longitudinally with respect to the machine running direction of the production plant 2 to an orientation transversely with respect to the machine running direction of the production plant 2. The plate 14 outputs the sanitary material piece 16 in the second transfer region 20 with a second orientation which is different than the first orientation, in a manner which is rotated about the vertical axis 17, here and preferably rotated about the vertical axis 17 by 90°.

Figure 4:
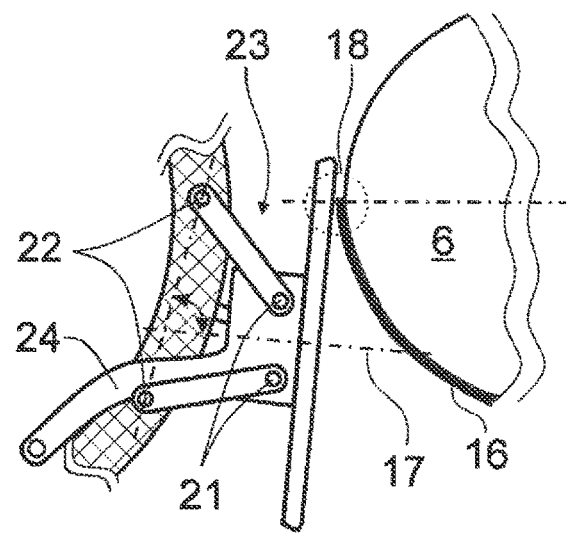
FIG. 4 shows the process of the compensation movement by way of example in an enlarged form.
Figure 4:
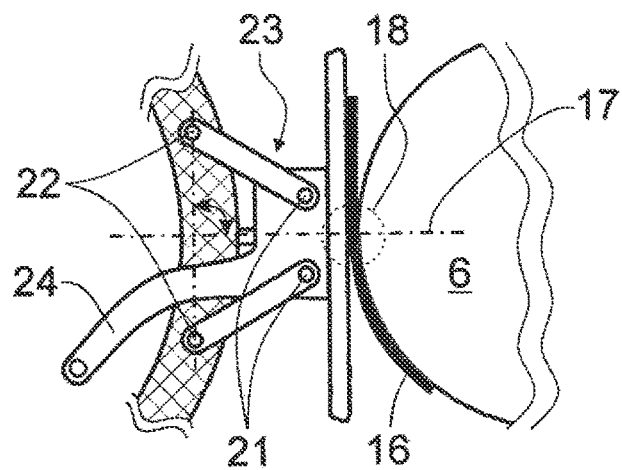
Figure 4:
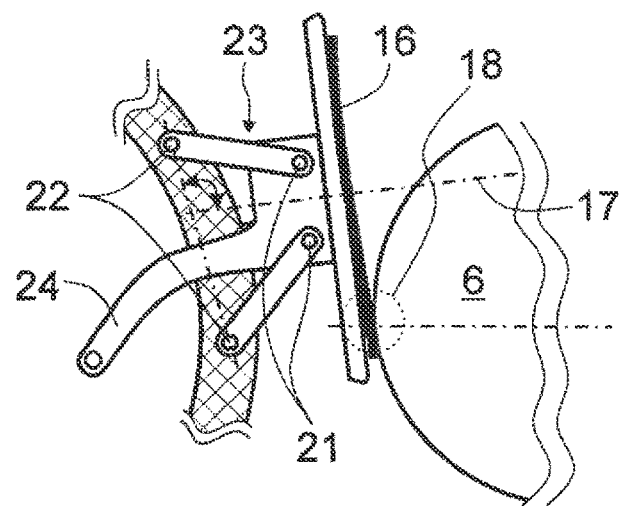

According to the proposal, during the receiving and/or outputting, the plate 14 carries out a non-linear compensation movement relative to the drum 12 with a radial movement component (see, in particular, FIG. 4). Here, the term "non-linear" means that the compensation movement per se, that is to say without consideration of the simultaneous rotation of the drum, is not a purely linear translation. The suction face 15 is therefore not displaced in a purely linear manner in one direction. It is an advantage here that a more complex movement can be implemented in a structurally simple manner and, at the same time, an improved adaptation is made possible to the prevailing mostly circular movement tracks. Here, the respective transfer of the sanitary material piece 16 can be optimized with regard to various factors by way of the acceptance of the more complex movement.

Firstly, the compensation movement can be adapted to a setpoint transfer path of an outputting or receiving unit, that is to say the cutting unit 6 or the repitch unit 8 here.

A geometrical rotational axis of the setpoint transfer path of the outputting or receiving unit will usually lie outside the setpoint transfer path of the turning apparatus 1. It is therefore preferably the case that the compensation movement comprises a rotation about a geometrical rotational axis, and that said geometrical rotational axis lies outside the setpoint transfer path of the turning apparatus 1. The geometrical rotational axis of the compensation movement can particularly preferably correspond to the geometrical rotational axis of the outputting or receiving unit, in particular of the cutting unit 6 or the repitch unit 8.

Secondly, in addition or as an alternative, an adaptation of the speed of the sanitary material piece 16 can take place if the outputting and the receiving unit do not have the same speed as the turning apparatus 1.

At the same time, the transfer angle between the suction face 15 and the sanitary material piece 16 can also be adapted.

Since rotational axes can additionally partially be implemented in a structurally simpler manner than linear axes, these advantages can be associated with structural advantages.

Here and preferably, the compensation movement has at least two components which run radially in opposite directions. Here, one side of the suction face 15 moves radially inward, and at the same time the other side moves radially outward.

As can be seen in the figures, the plate 14 or the suction face 15 reaches the first transfer region 18 from below in a manner which is tilted in one direction, and leaves it at the top in a manner which is tilted in the other direction. As a result, the plate 14 can be adapted to the transfer region 18, 20 by way of a type of nodding movement. The compensation movement is also shown in the second transfer region 20 in FIG. 3. On account of the rotation of the suction face 15 and the correspondingly smaller proportions, it is correspondingly less expansive there. Here and preferably, the entire plate 14 carries out the compensation movement, but it is likewise advantageously conceivable that only one part of the plate 14, in particular the suction face 15, carries out the compensation movement.

Figure 3:
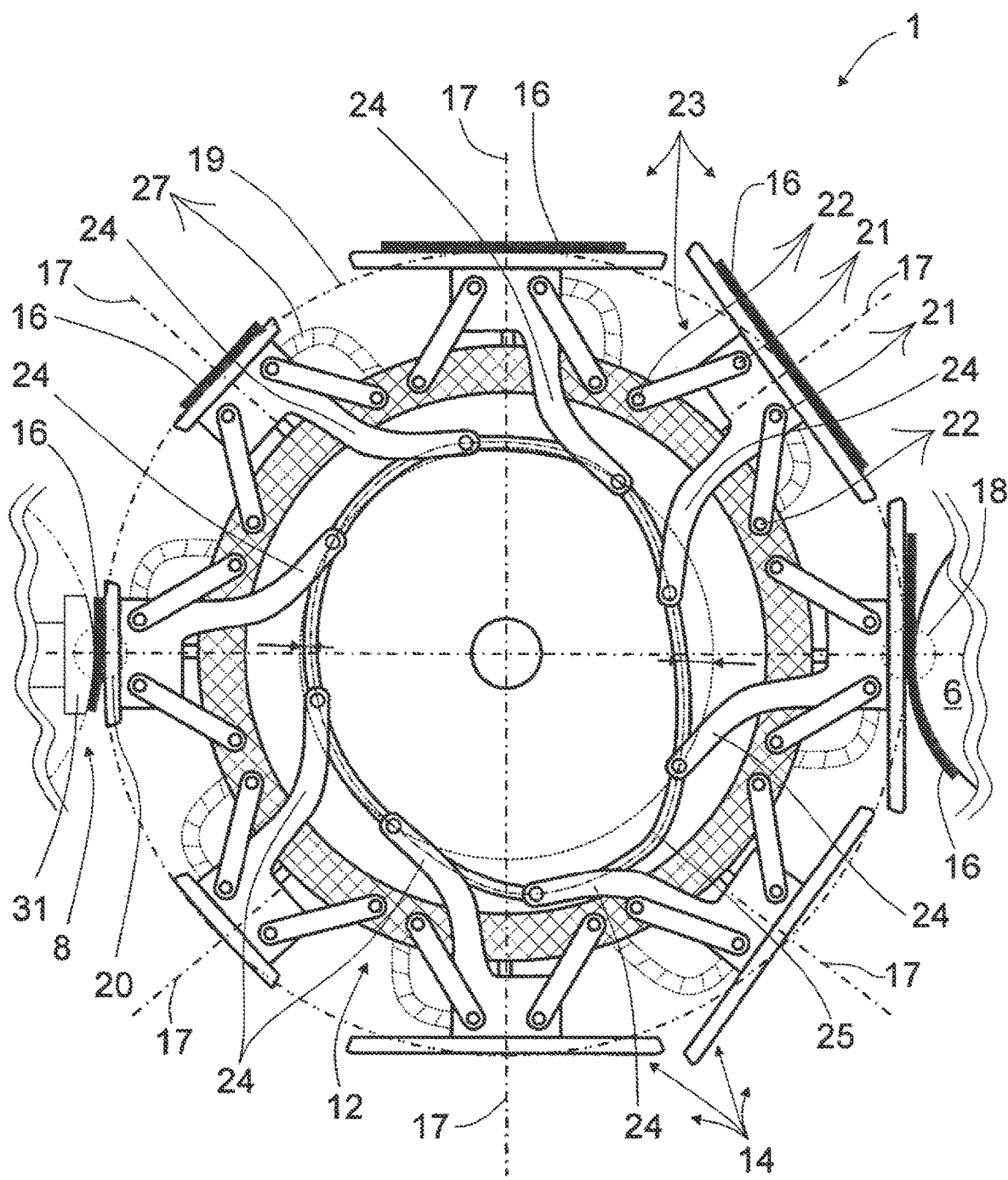
FIG. 3 shows the inner workings of the turning apparatus according to the proposal.

Here and preferably, the compensation movement of the plate 14 additionally has a movement component in the circumferential direction about the drum rotational axis 11. In addition or as an alternative, the compensation movement can comprise a rotational movement of the plate 14 about a first geometrical rotational axis 21. The compensation movement preferably additionally comprises a rotation of the first rotational axis 21 about a second rotational axis 22. This is illustrated in FIGS. 3 and 4, the first rotational axis 21 and the second rotational axis 22 being provided with designations for the sake of simplicity only in the case of one plate 14. Further preferably, the compensation movement can comprise a further rotation about a further first rotational axis 21 and a further rotation of the further first rotational axis 21 about a further second rotational axis 22. Here, said rotations can take place at least partially at the same time or sequentially. The first and the second rotational axis 21, 22 are preferably parallel, but not coaxially, with respect to the drum rotational axis 11 and/or with respect to one another. The term "rotation" always means a rotation with a degree of freedom about a geometrical rotational axis. The movement component of the compensation movement in the circumferential direction is understood relative to the drum 12, that is to say it differs from the already existing rotation of the drum 12.

Here and preferably, the compensation movement is a continuous movement which therefore comprises neither a stop nor an abrupt directional change. After the compensation movement has ended, however, resetting with a directional change can take place.

It can be provided that the plate 14 is coupled to the drum 12 in such a way that the progress of the compensation movement is dependent, in particular solely, on a rotational angle of the drum 12 about the drum rotational axis 11. Here and preferably, said coupling is mechanical. Here and preferably, this likewise means that the progress of the compensation movement is dependent on the rotational angle of the plate 14 about the drum rotational axis 11. Said rotational angle is fundamentally dependent on the respective plate 14. It is provided here and preferably that each plate 14 carries out the same compensation movement in the case of the corresponding rotational angle.

In the following text, the realization of the performance of the compensation movement is described, which can likewise best be gathered from the illustration in FIG. 3. Here and preferably, the plate 14 forms, with the drum 12, a coupling mechanism 23. Here, the term "coupling mechanism" is based expressly on the definition which is customary in mechanical engineering. Here and preferably, the coupling mechanism 23 is a four-member coupling mechanism 23, in particular a four-bar mechanism. The coupling mechanism 23 can be a planar coupling mechanism 23, the plane of which is then preferably oriented at an angle, in particular at a right angle, with respect to the drum rotational axis 11. In the case of a planar coupling mechanism, the axes of the joints of the coupling mechanism are oriented parallel to one another, with the result that the movements of the coupling mechanism take place in one plane. As shown, the plate 14 preferably forms a member of the coupling mechanism 23, and is connected by way of two further members to the drum 12 which likewise forms a member of the coupling mechanism 23. Here and preferably, that part of the plate 14 which forms the member of the coupling mechanism 23 does not rotate with the suction face 15 about the vertical axis 17.

In particular for the actuation of the coupling mechanism 23, the plate 14 can be coupled by means of a guide member 24 to a cam disk 25, with respect to which the plate 14 can be moved. The compensation movement is then caused by way of the coupling of the plate 14 via the guide member 24 which is guided by the cam disk 25 to the cam disk 25. As an alternative, however, a passive, external guidance of the compensation movement would also be conceivable, for example. Here and preferably, the cam disk 25 is arranged about the drum rotational axis 11. The cam disk 25 can guide the guide member 24 on one side or on two sides; correspondingly, the guide member 24 can rest on it, in particular in a spring-loaded manner, or can run in a guide of the cam disk 25, as shown in FIG. 3. FIG. 3 also illustrates the different spacings of the guide track of the cam disk 25 from an ideal circular path in the case of receiving and outputting of the sanitary material piece 16, which spacings occur as a result of the rectangular, but not square, shape of the sanitary material pieces 16 and the suction face 15 in combination with the rotation of the suction face 15.

For example, an actuation of the plate 14 by means of a crank mechanism or in some other way would also likewise advantageously be conceivable. Here and preferably, the cam disk 25 does not rotate with the drum 12 about the drum rotational axis 11, but rather is at a standstill, in particular.

In one exemplary embodiment which is not shown, the compensation movement can be a rotation of the plate 14 about a geometrical rotational axis which preferably runs parallel, but not coaxially, with respect to the drum rotational axis 11. This variant would then be accompanied by a change of the speed of the sanitary material piece 16.

As can be seen in FIG. 3, the guide member 24 can be coupled rigidly to the plate 14. As an alternative, for example and likewise preferably, one modification is conceivable, in the case of which the guide member 24 is coupled by means of a joint to the plate 14 and/or the cam disk 25, in particular such that it can be displaced there. In yet another variant, the guide member 24 might also be a member of the coupling mechanism 23 or might be connected to the latter.

Here and preferably, the receiving and/or the outputting of the sanitary material piece 16 takes place over the full surface area with a constant transfer spacing. Here, the transfer spacing relates to the spacing between the respective receiving or outputting part of the plate 14 and the cutting roller 6 or the repitch unit 8 or another conceivable receiving or outputting component of the production plant 2 otherwise. Over the full surface area means here that, although the sanitary material piece 16 is transferred piece by piece, there is, however, a linear contact with the plate 14. The constant transfer spacing is substantially constant and deviates at most by 5%, preferably at most by 1%, further preferably at most by 0.5%.

In addition or as an alternative, a speed of the sanitary material piece 16 remains constant during the receiving and/or outputting of the sanitary material piece 16, and deviates at most by 5%, preferably at most by 1%, further preferably at most by 0.5%. Here, a deflection of the sanitary material piece 16 is provided; both the receiving and the outputting element have the same speed here, however.

In the embodiment which is shown and to this extent is particularly preferred, the suction face 15 of the plate 14 is planar along its first and/or second orientation.

Here and preferably, a part of the suction face 15 of the plate 14, which part is situated in the first transfer region 18, remains radially within the setpoint transfer path 19 on account of the compensation movement during the receiving. In addition or as an alternative, a part of the suction face 15 of the plate 14, which part is situated in the second transfer region 20, can remain radially within the setpoint transfer path 19 on account of the compensation movement during the outputting. Furthermore, in addition or as an alternative, the suction face 15 along the first and/or second orientation can run not along the setpoint transfer path 19, in particular in such a way that the suction face 15 remains within the respective transfer region 18, 20 in the first and/or second transfer region 18, 20 only on account of the compensation movement. In the illustration in FIG. 3, this can be seen by virtue of the fact that, as viewed from the bottom upwards on the right-hand side, the suction face 15 dips into the transfer region 18 with the front end in the case of a movement in the counterclockwise direction, and then tilts upward via a tilting movement via the coupling mechanism 23 in such a way that, at the end, the rear end in the transfer region 18 is within the setpoint transfer path 19. Here and preferably, a similar compensation movement is also carried out in the second transfer region 20.

In order that the sanitary material piece 16 is not deflected by way of the vacuum of the suction face 15 during the transfer, it can be provided that the suction face 15 comprises a plurality of suction segments 15a which can preferably be actuated individually. Here and preferably, the actuation of the suction segments 15a takes place in such a way that the suction segments 15a are actuated in a manner which is dependent on the rotational angle of the drum 12 and/or a progress of the compensation movement. Said actuation can take place electronically, but in principle also mechanically.

Here and preferably, the suction segments 15a of the suction face 15 are rotated with the suction face 15 about the vertical axis 17. It is preferably provided, however, that, in particular on that side of the suction face 15 which faces away from the sanitary material piece 16, suction segment feed lines (not shown) are provided which are connected in a vacuum-conducting manner to the suction segments 15a of the suction face 15. It is then preferably provided that the suction segment feed lines are not rotatable about the vertical axis 17.

Therefore, the assignment of the suction segment feed lines to the suction segments 15a changes during the rotation of the suction face 15. The actuation is adapted correspondingly.

In addition or as an alternative, it can be provided that the suction segments 15a are loaded with compressed air during the transfer of the sanitary material piece 16, preferably in a correspondingly sequential manner, in order that the vacuum is deactivated more rapidly.

Here and preferably, at least four, further preferably precisely four, suction segments 15a and/or suction segment feed lines are provided.

Here and preferably, the drum 12 has a drive shaft 26 for the generation of the rotation of the drum 12 about the drum rotational axis 11. The drive shaft 26 is concentric, in particular, with respect to the drum rotational axis 11. The drive shaft 26 can be configured as a hollow shaft, with the result that the vacuum can be conducted from a vacuum source through the drive shaft 26 to the suction face 15. Here, the hollow shaft itself can conduct the vacuum or can comprise a hose or the like. The vacuum is preferably conducted via tube or hose connections 27 which lead out of the drive shaft 26 to the suction face 15 and, in particular, to the suction segments 15a.

The drive shaft 26 can be mounted on a carrier 28 which has, in particular, two arms. The turning apparatus 1, in particular the carrier 28 here, is preferably self-supporting.

Here and preferably, the drum 12 can have two disks 13 which are spaced apart, run at an angle, in particular at a right angle, with respect to the drum rotational axis 11, and to which the plate 14 is coupled in each case.

As has already been mentioned, the turning apparatus 1 preferably has a plurality of, in particular at least three, further preferably at least six, even further preferably precisely eight, identical plates 14. Very generally, the plate 14 can be coupled to the drum 12 in such a way that the plate 14 rotates with the drum 12 without slip.

According to a further teaching which is given independent significance, a production plant 2 for sanitary products, in particular adult or baby diapers, is proposed. The production plant 2 has a turning apparatus 1 according to the proposal. Reference may be made to all comments with respect to the turning apparatus 1 according to the proposal. Here and preferably, said production plant 2 can produce a plurality of formats of the sanitary products.

The production plant 2 can be best gathered from the illustration in FIG. 2. Here and preferably, the production plant 2 cuts sanitary material pieces 16 from an endless sanitary material web 3. Here and preferably, the sanitary material is an absorbent material, with the result that the sanitary material pieces 16 are, in particular, absorbent cores. Furthermore, the production plant 2 can cut carrier material pieces from an endless carrier material web 29, which carrier material pieces are here and preferably waist bands. The production plant 2 produces the sanitary products by way of connection of the sanitary material pieces 16 and the carrier material 9. The cutting of the endless carrier material web 29 can take place before or after the connection to the sanitary material pieces 16. Here, the term "endless" means merely that the production plant 2 is designed in such a way that the length of the corresponding web can be great in comparison with the length of a corresponding individual piece.

The production plant 2 is shown in FIG. 2 from right to left in terms of the production sequence. It can have a feed means for the sanitary material web 3, which is shown on the extreme right here. The sanitary material web 3 is preferably fed via a first transport roller 4, which rotates at a first speed v1, to a cutting roller 6, which rotates at a second speed v2. The sanitary material web 3 is cut into sanitary material pieces 16 on the cutting roller 6 by way of a cutting unit 7. On account of the rollers 4, 6 which rotate at different speeds v1, v2, slip of the sanitary material web 3 occurs upstream of the cutting unit 7. In the cutting unit 7, the sanitary material pieces 16 are accelerated on the cutting roller 6 in such a way that they are set to the spacing between the plates 14 of the turning apparatus 1. Said spacing at the same time specifies the maximum format to be produced of sanitary material pieces 16. The sanitary material pieces 16 are transferred in the first transfer region 18 from the cutting roller 6 to the turning apparatus 1. The turning apparatus 1 turns the sanitary material pieces 16 about the vertical axis 17, here and preferably by 90°. The turning apparatus 1 can then transfer the sanitary material pieces 16 to a repitch unit 8 which accelerates or brakes the sanitary material pieces 16 to a third speed v3. The production plant 2 can have a carrier roller 30 which rotates at the third speed v3 and on which the carrier material 9 (here and preferably, the carrier material web 29 or carrier material pieces) is guided. The repitch unit 8 transfers the sanitary material pieces 16 to the carrier roller 30 and deposits them on the carrier material 9. Here and preferably, some or all of the rollers are likewise equipped with vacuum, in order to hold the respective material. This can likewise apply to the repitch unit 8. Here and preferably, the latter has a plurality of transfer plates 31 which rotate independently of one another, in order to accelerate the sanitary material.

The invention claimed is:

1. A turning apparatus for a production plant for sanitary products, the turning apparatus comprising:
    a drum configured to rotate about a geometrical drum rotational axis; and
    at least one plate that is spaced apart radially from the drum rotational axis and is coupled to the drum;
    wherein the plate includes a suction face for transporting a sanitary material piece,
    wherein the suction face is configured to hold the sanitary material piece by means of a vacuum during transport,
    wherein the plate has a geometrical vertical axis that runs radially with respect to the drum rotational axis,
    wherein the plate is configured to receive the sanitary material piece with a first orientation about the vertical axis in a first transfer region,
    wherein the plate is configured to transport the sanitary material piece from the first transfer region to a second transfer region along a setpoint transfer path that runs in a circumferential direction around the drum rotational axis,
    wherein the suction face is configured to be rotated with the sanitary material piece about the vertical axis during the transport,
    wherein the plate is configured to output the sanitary material piece in the second transfer region such that the sanitary material piece has a second orientation which is different than the first orientation about the vertical axis,
    wherein, during the receiving and/or outputting, the plate is configured to carry out a non-linear compensation movement relative to the drum with a radial movement component,
    wherein the plate is coupled to a cam disk by means of a guide member, and
    wherein the compensation movement is caused by way of the coupling of the plate via the guide member to the cam disk.

2. The turning apparatus as claimed in claim 1, wherein the compensation movement of the plate additionally has a movement component in the circumferential direction about the drum rotational axis, and/or wherein the compensation movement comprises a rotational movement of the plate about a first geometrical rotational axis.

3. The turning apparatus as claimed in claim 1, wherein the plate is coupled to the drum in such a way that progress of the compensation movement is dependent on a rotational angle of the plate about the drum rotational axis.

4. The turning apparatus as claimed in claim 1, wherein the plate forms, with the drum, a coupling mechanism.

5. The turning apparatus as claimed in claim 1, wherein the compensation movement is a rotation of the plate about a geometrical rotational axis which runs parallel, but not coaxially, with respect to the drum rotational axis.

6. The turning apparatus as claimed in claim 1, wherein the receiving and/or the outputting of the sanitary material piece take/takes place over a full surface area at a constant transfer spacing, and/or wherein a speed of the sanitary material piece remains constant during the receiving and/or outputting of the sanitary material piece.

7. The turning apparatus as claimed in claim 1, wherein the suction face of the plate is planar along its first and/or second orientation.

8. The turning apparatus as claimed in claim 1, wherein a part of the suction face of the plate that is situated in the first transfer region remains radially within the setpoint transfer path on account of the compensation movement during the receiving, and/or wherein a part of the suction face of the plate that is situated in the second transfer region remains radially within the setpoint transfer path on account of the compensation movement during the outputting, and/or wherein the suction face does not run along the setpoint transfer path along the first and/or second orientation.

9. The turning apparatus as claimed in claim 1, wherein the suction face comprises a plurality of suction segments.

10. The turning apparatus as claimed in claim 1, wherein the drum has a drive shaft for rotating the drum about the drum rotational axis.

11. The turning apparatus as claimed in claim 1, wherein the drum has two disks which are spaced apart, run at an angle with respect to the drum rotational axis, and to which the plate is coupled in each case.

12. The turning apparatus as claimed in claim 1, wherein the turning apparatus has a plurality of identical plates, and/or wherein the plate is coupled to the drum in such a way that the plate rotates with the drum without slip.

13. A production plant for sanitary products, wherein the production plant comprises a turning apparatus according to claim 1.

14. The production plant for sanitary products as claimed in claim 13, wherein the production plant further comprises a device for cutting sanitary material pieces from an endless web of sanitary material, wherein the production plant further comprises a device for cutting carrier material pieces from an endless web of carrier material, and wherein the production plant is configured to manufacture the sanitary products by connecting the sanitary material pieces and the endless web of carrier material or by connecting the sanitary material pieces and the carrier material pieces.

15. The production plant for sanitary products as claimed in claim 14, wherein the production plant has a feed means for the web of sanitary material, wherein the web of sanitary material is fed via a first transport roller that is configured to rotate at a first speed to a cutting roller that is configured to rotate at a second speed, wherein the production plant is configured to cut the web of sanitary material on the cutting roller by way of a cutting unit into the sanitary material pieces, wherein the production plant is configured to accelerate the sanitary material pieces on the cutting roller to the second speed, wherein the turning apparatus is configured to rotate at the second speed, wherein the production plant is configured to transfer the sanitary material pieces in the first transfer region from the cutting roller to the turning apparatus, wherein the turning apparatus is configured to rotate the sanitary material pieces about the vertical axis by 90 degrees, wherein the turning apparatus is configured to transfer the sanitary material pieces to a repitch unit that accelerates or brakes the sanitary material pieces to a third speed, wherein the production plant has a carrier roller that is configured to rotate at the third speed and on which the endless web of carrier material or the carrier material pieces are guided, and wherein the repitch unit is configured to transfer the sanitary material pieces to the carrier roller and deposit the sanitary material pieces on the endless web of carrier material or the carrier material pieces.

* * * * *